United States Patent [19]

Krieg et al.

[11] Patent Number: 5,053,223

[45] Date of Patent: Oct. 1, 1991

[54] **PROCESS AND AGENTS FOR CONTROL OF WHITE COFFEE-LEAF MINERS, ESPECIALLY *PERILEUCOPTERA COFFEELLA***

[75] Inventors: Wolfgang Krieg, Weingarten; Hansgeorg Ernst, Speyer; Ernst Buschmann, Ludwigshafen; Wittko Francke, Reinbek; Wolf Engels, Tuebingen, all of Fed. Rep. of Germany

[73] Assignee: BASF Aktiengesellschaft, Ludwigshafen, Fed. Rep. of Germany

[21] Appl. No.: 379,715

[22] Filed: Jul. 13, 1989

Related U.S. Application Data

[63] Continuation of Ser. No. 171,387, Mar. 21, 1988, abandoned.

[30] Foreign Application Priority Data

Mar. 26, 1987 [DE] Fed. Rep. of Germany ....... 3709922

[51] Int. Cl.$^5$ ...................... A01N 25/00; A01N 27/00
[52] U.S. Cl. ........................................ 424/84; 514/762
[58] Field of Search ........................... 424/84; 514/762

[56] References Cited

U.S. PATENT DOCUMENTS 4,853,217 8/1989 Francke ................................ 424/84

FOREIGN PATENT DOCUMENTS 3615854 11/1987 Fed. Rep. of Germany .

OTHER PUBLICATIONS

Chemical Abstracts No. 193131g, vol. 106, No. 23, 1987.
Francke (1984 Advances in Invertebrate Reproduction 3), p. 493.
Baker et al., (1978/9) Aliphatic and Related Natural Product Chemistry, vol. 2, pp. 46–49.
Klun (1984) Bioregulators for Pest Control, p. 381.
Carde et al., In Techniques in Pheromone Research, Hummel et al. eds.

*Primary Examiner*—Frederick E. Waddell
*Assistant Examiner*—Russell Travers
*Attorney, Agent, or Firm*—Keil & Weinkauf

[57] ABSTRACT

5,9-Dimethylpentadecane (I) and 5,9-dimethylhexadecane (II) and their use in agents for the control of the white coffee-leaf miner, *Perileucoptera coffeella*, particularly by the confusion technique.

10 Claims, No Drawings

PROCESS AND AGENTS FOR CONTROL OF WHITE COFFEE-LEAF MINERS, ESPECIALLY *PERILEUCOPTERA COFFEELLA*

This application is a continuation of application Ser. No. 171,387, filed on Mar. 21, 1988, now abandoned.

The white coffee-leaf miner *Perileucoptera coffeella* (Guer. Menev., 1842), a microlepidopter of the family Lyonetiidae, is the major pest in the coffee plantations of Central and South America; it is also endemic in the West Indies and in Madagascar. Closely related species of the genus *Leucoptera*, *L. meyricki*, *L. coma*, and *L. caffeina*, occur in Central Africa-cf. Kranz, Schmutterer, & Koch, *Diseases, Pests, and Weeds in Tropical Crops*, (1977); Hill, *Agricultural Pests of the Tropics and their Control*, (1975).

These pests are economically significant because their larvae spend their lives burrowing in the palisade layer of coffee leaves, which can lead to considerable destruction of assimilatory surface areas; the resulting leaf fall causes large reductions in yields, particularly if it occurs a few weeks before the cherries are harvested. The leaf damage can also result in weakening of fruiting branches or even of the whole tree, and recovery does not take place until the following season.

The weather greatly affects development of the pests: dry weather promotes infestation, and several generations can evolve in a single season.

These leaf miners are not easy to control because they live unobtrusively: the young caterpillars burrow by themselves in round individual tunnels, pupation takes place in cocoons on the undersides of the leaves. It is possible to use organo-phosphorus ester insecticides which have a systemic action, or pyrethroids, but all such insecticides are nonselective, and many of them are toxic to warm bloods. Up till now systematic control has not been possible because of the lack of reliable methods of recognizing infestation or of selective control.

It is known that female moths secrete a pheromone that acts as a sexual attractant when they are ready for mating, and that this allows them to be located by males of the same species. This phenomenon can be utilized for crop protection in three different ways.

Pheromone traps suspended in areas of potential infestation are baited with synthetic pheromones. The catch of male moths indicates the presence of pests, gives a measure of the degree of infestation, and is a guide to the best time to undertake pest-control measures.

The pheromone can be coupled with an insecticide, which can be in the trap or in the immediate vicinity. This interception technique enables most of the male moth population, which is enticed from large distances, to be killed. Disturbance of the biotope is reduced to acceptable levels.

The third method of pest control is that of saturating the atmosphere with the pheromone or a substance that acts similarly as a sexual attractant. The males can no longer locate individual females, so no mating takes place. In this case the attractant is released in large quantities all over the plantation to be protected, filling the air uniformly and disorientating the males, which detect the scent everywhere they go.

Even in the last method of utilizing pheromones the quantities employed are relatively small, often only a small fraction of the amount of classical insecticides usually applied—cf. Birch ed., *Pheromones*, North Holland Publishing Co. (1974). Here we have an extremely selective, nontoxic method of pest control that spares organisms that are not the target—in particular useful organisms—to the greatest possible extent.

We have found that preparations containing 5,9-dimethylpentadecane (I) or 5,9-dimethylhexadecane (II) or both are effective pheromones in particular for *Perileucoptera coffeella*.

The present invention thus relates to agents that contain 5,9-dimethylpentadecane or 5,9-dimethylhexadecane or both for enticing or confusing male insects, in particular those of the species *Perileucoptera coffeella*.

A possible route for the synthesis of the novel compounds is illustrated by the Example given below. It yields a mixture of stereoisomers if racemic starting compounds are used, but sterically homogeneous products are obtained from homogeneous starting materials.

1-Bromo-3-chloro-2-methylpropane is a unit used repeatedly. It is first reacted with halo(propyl)magnesium in the presence of a tetrahalocuprate of an alkali metal, preferably dilithium tetrachlorocuprate, to form 1-chloro-2-methylhexane. This is treated with magnesium to form the Grignard compound, which yields 3-methyl-1-heptanol by treatment with formaldehyde. The alcohol is brominated by one of the usual reagents—for instance, hydrobromic acid, phosphorus tribromide, triphenylphosphine and bromine, triphenylphosphine and tetrabromoethane, or triphenylphosphine and N-bromosuccinimide—forming 1-bromo-3-methylheptane; it could instead be chlorinated. The corresponding Grignard compound is formed with magnesium and treated with 1-bromo-3-chloro-2-methylpropane in the presence of dilithium tetrachlorocuprate, yielding 1-chloro-2,6-dimethyldecane. This is finally converted to (5 RS, 9 RS)-5,9-dimethylpentadecane by treating the Grignard compound with 1-bromopentane, or similarly to the 5,9-dimethylhexadecane by treatment with 1-bromohexane.

The sequence of operations can be altered if chemical considerations make this desirable.

EXAMPLE

Preparation of 1-chloro-2-methylhexane (3)

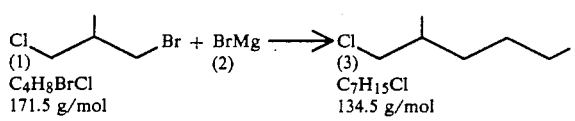

Magnesium turnings (29.3 g, 1.21 mol) are covered with tetrahydrofuran (140 ml) and a solution of 1-bromopropane (147.6 g, 1.2 mol) in tetrahydrofuran (300 ml) is added dropwise, the temperature being maintained at from 40° C. to 50° C. More tetrahydrofuran (200 ml) is added and the mixture is stirred at a temperature of 40° C. for 1 h. The mixture is cooled to −25° C., a solution of 1-bromo-3-chloro-2-methylpropane (103 g, 0.60 mol) in tetrahydrofuran (300 ml) and molar dilithium tetrachlorocuprate in tetrahydrofuran (31.6 ml) are added, and the mixture is stirred at a temperature of −20° C. for 2 h, at 0° C. for 2 h, and at room temperature overnight. The mixture is cooled in an ice bath, hydrolyzed with saturated ammonium chloride solution, and extracted several times with ether. The extract is washed with saturated ammonium chloride solution, dried over sodium sulfate, and evaporated down.

The product, weighing 75.4 g, yields 58 g of the C₇-alkyl chloride (3) of purity from 98% to 99% by distillation at 51° C. under a pressure of 30 mbar. The yield is 71.9%.

Preparation of 3-methyl-1-heptanol (4)

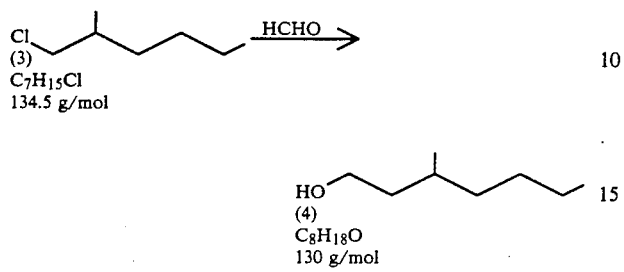

Magnesium turnings (2.0 g, 82.3 mmol) are etched with iodine, and 1 ml of a solution of 96% 1-chloro-2-methylhexane (11 g, 78.5 mmol) in tetrahydrofuran (10 ml) is added at 60° C. The reaction is started by the addition of 1,2-dibromoethane (0.2 ml), then the rest of the solution of 1-chloro-2-methylhexane is added dropwise. After dilution with tetrahydrofuran (15 ml) the mixture is stirred under reflux for 2.5 h. Gaseous formaldehyde is passed through the solution, whose temperature is kept at from 40° C. to 50° C. The mixture is stirred for a further 1 h at room temperature, then 30% sulfuric acid (10 ml) is added to hydrolyze the Grignard compound. The mixture is steam distilled and the distillate is extracted several times with ether. The extract is washed with sodium chloride solution, dried over sodium sulfate, and evaporated down.

The product, weighing 10.8 g, contains 74% of the C₈-alcohol (4). The yield is 78.3%.

Distillation of the crude product under a pressure of 0.3 mbar yields 7.95 g of the alcohol (4) of purity 95%, which passes over at 80° C., a yield of 74.0%.

Preparation of 1-bromo-3-methylheptane (5)

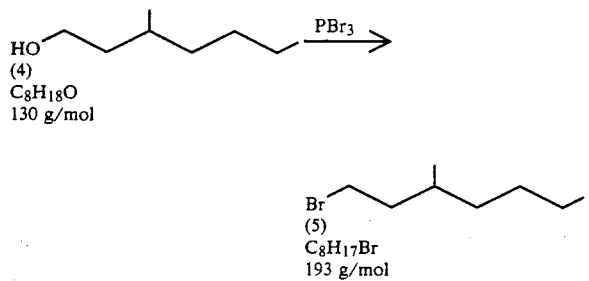

Phosphorus tribromide (10.44 g, 38.5 mmol) is added dropwise to 95% 3-methyl-1-heptanol (7.7 g, 56.3 mmol) at 0° C. and the mixture is stirred for 5 h at 100° C. The mixture is allowed to cool, poured onto ice, and extracted several times with hexane. The extract is washed with sodium carbonate solution, dried over magnesium sulfate, and evaporated down.

The product weighs 11.2 g and contains 93% of the C₈-alkyl bromide (5)—determined by gas chromatography—a yield of 95.9%. Distillation at 110° C. under a pressure of 30 mbar with an Allihn condenser gives 10.31 g of the C₈-alkyl bromide in 97% purity, a yield of 92.0%.

Preparation of 1-chloro-2,6-dimethyldecane (6)

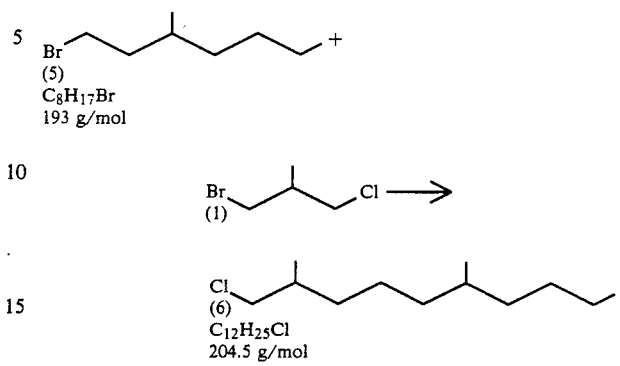

Magnesium (1.14 g, 47 mmol) is covered with tetrahydrofuran (7 ml), 97% 1-bromo-3-methylheptane (9 g, 45.2 mmol) dissolved in tetrahydrofuran (16 ml) is added dropwise at 50° C., and the mixture is stirred for 1 h at 40° C. The mixture is cooled to −30° C. and 1-bromo-3-chloro-2-methylpropane (6.8 g, 39.7 mmol) dissolved in tetrahydrofuran (8 ml) is added. After addition of 0.5M dilithium tetrachlorocuprate in tetrahydrofuran (5.5 ml) the mixture is stirred for 2 h at −30° C., 2 h at 0° C., and overnight at room temperature. The mixture is cooled in the ice bath and hydrolyzed with saturated ammonium chloride solution, then extracted several times with ether. The extract is washed with saturated ammonium chloride solution, dried over magnesium sulfate, and evaporated down. The residue is distilled under a pressure of 0.5 mbar at up to 120° C., giving 5.38 g of the C₁₂-alkyl chloride (6) of purity 93%, a yield of 62.2% based on the amount of C₈-alkyl bromide (1).

Preparation of 5,9-dimethylpentadecane (7)

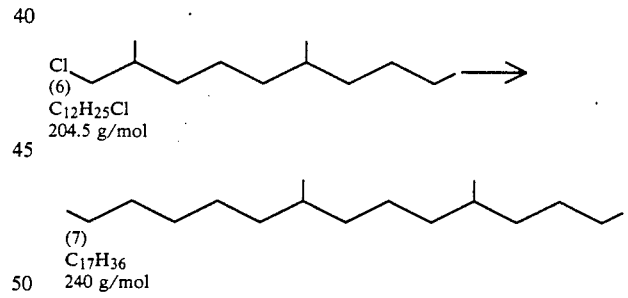

Magnesium (0.54 g, 22.2 mmol) is etched with iodine and 0.5 ml of a solution of 93% 1-chloro-2,6-dimethyldecane (4.5 g, 20.7 mmol) in tetrahydrofuran (4 ml) is added at 60° C. After the reaction has been started by addition of a drop of 1,2-dibromoethane the rest of the solution is added dropwise. The mixture is diluted with tetrahydrofuran (4 ml) and stirred under reflux for 2.5 h, then cooled to −20° C. 1-Bromopentane (3.8 g, 25 mmol) in tetrahydrofurane (4 ml) and 0.5M dilithium tetrachlorocuprate in tetrahydrofuran (3 ml) are added, and the mixture is stirred at −20° C. for 2 h, at 0° C. for 2 h, and at room temperature overnight. Subsequent treatment with ammonium chloride solution and distillation gives 3.22 g of 5,9-dimethylpentadecane, a yield of 64.8% based on the amount of C₁₂-alkyl chloride.

The novel active ingredients can be incorporated in either liquid or solid preparations.

Possible solvents are compounds that boil at high temperatures, which can be aromatic, aliphatic, or cycloaliphatic. Hydrocarbons and esters, ethers, or ketones are especially suitable. Typical of these classes are, for example, xylene, methylnaphthalenes, mineral oils, cyclohexanone, ethoxyethyl acetate, isophorone, and dibutyl phthalate.

Effectiveness can be prolonged by dissolving the active ingredient in vegetable, animal, or synthetic oils or fats or in other solvents that slow down evaporation and themselves have low vapor pressures, for instance dioctyl phthalate.

Solid preparations are obtained by absorbing or adsorbing the active substance on natural or synthetic solid carriers such as rubber, cork, cellulose, plastics, powdered charcoal, sawdust, silicates, pumice, burnt clay, and similar materials. Prolonged, uniform emission into the atmosphere can also be achieved by enclosing the active ingredient in plastic capsules or other forms of container or in multi-layer plastic flakes, through which it can diffuse. Particularly uniform vapor concentrations can be maintained over long periods by allowing the active ingredient to pass through narrow openings of suitable receptacles, such as capillary tubes or other vessels.

The amount of active ingredient in these preparations can vary within wide limits. For instance, the ratio of active ingredient to additive can be from 10:1 to 1:1000. When the active ingredient is enclosed in capsules or the like it can be used undiluted, and its mass fraction can be very high—up to 90%. In general however the concentration of active ingredient sufficient to obtain the desired effect on the males of the genus *Perileucoptera* is very small. The preferred ratio of active ingredient to additive is from 1:3 to 1:100.

It is also possible to apply the active ingredient in comparatively high concentrations so as to disorientate and confuse the males to such an extent that they not only have difficulty in locating the females but also are incapable of mating. For this purpose the best preparations are those that give off active ingredient gradually, for instance those based on nonvolatile carriers such as rubber, cellulose, waxes, or polymers, those based on solvents of low volatility that inhibit evaporation, such as mineral oils, and those in which the active ingredient is held in capsules, capillaries, or the like and escapes by diffusion. In this case the amounts of active ingredient and additive are in the ratio of from 10:1 to 1:1000.

Outdoor trials in a region of potential infestation by *Perileucoptera coffeella* provide evidence of the biological effectiveness of the claimed pheromone components.

We claim:

1. 5,9-Dimethylpentadecane.

2. 5,9-Dimethylhexadecane.

3. An attractant composition for white coffee-leaf miner *Perileucoptera coffeella* which comprises: a liquid or solid carrier and an effective amount of one or both of 5,9-dimethylpentadecane or 5,9-dimethylhexadecane as the active ingredient.

4. A method of attracting and trapping the male white coffee-leaf miner *Perileucoptera coffeella* which comprises: placing traps containing an effective amount of one or both of 5,9-dimethylpentadecane or 5,9-dimethylhexadecane in areas of *Perileucoptera coffeella* infestation or potential infestation, which compounds act as sexual attractants for male *Perileucoptera coffeella* moths; and thereafter determining the degree of infestation in the area by measuring the catch of male *Perileucoptera coffeella* moths.

5. A method of preventing male white coffee-leaf miner *Perileucoptera coffeella* moths from locating female *Perileucoptera coffeella* moths for mating purposes which comprises: releasing into the atmosphere in an area of infestation or potential infestation of the white coffee-leaf miner *Perileucoptera coffeella* as a sexual attractant for male *Perileucoptera coffeella* moths an effective amount of one or both of 5,9-dimethylpentadecane or 5,9-dimethylhexadecane to confuse the male moths.

6. The method of claim 4, wherein the sexual attractants are combined in the traps with an insecticide which kills the trapped male *Perileucoptera coffeella* moths.

7. The method of claim 5, wherein the attractant is 5,9-dimethylpentadecane.

8. The method of claim 6, wherein the attractant is 5,9-dimethylpentadecane.

9. The method of claim 6, wherein the attractant is 5,9-dimethylhexadecane.

10. The method of claim 5, wherein the attractant is 5,9-dimethylhexadecane.

* * * * *